United States Patent [19]

Guigan

[11] Patent Number: 4,462,964
[45] Date of Patent: Jul. 31, 1984

[54] CONDITIONING DEVICE FOR PREPARING MULTIPLE ANALYSES

[76] Inventor: Jean Guigan, 9 rue Jean Mermoz, 75008 Paris, France

[21] Appl. No.: 457,317

[22] Filed: Jan. 11, 1983

[30] Foreign Application Priority Data

Jan. 14, 1982 [FR] France ............................... 82 00529

[51] Int. Cl.³ ...................... G01N 21/07; G01N 1/10; G01N 33/50; B04B 11/00
[52] U.S. Cl. ................................. 422/102; 422/72; 436/45; 436/165; 436/809; 356/427; 356/246; 435/293; 494/16
[58] Field of Search ...................... 422/55, 58, 61, 72, 422/99, 100, 102, 104; 436/45, 165, 808, 809; 435/293, 301, 300, 312; 356/427, 246

[56] References Cited

U.S. PATENT DOCUMENTS

| 3,532,470 | 9/1970 | Rochte ................................. 422/61 |
| 3,540,858 | 11/1970 | Rochte et al. ........................ 422/61 |
| 3,547,547 | 12/1970 | Anderson ............................. 356/197 |
| 4,076,592 | 2/1978 | Bradley ........................ 195/103.5 K |
| 4,314,968 | 2/1982 | Guigan ................................. 422/64 |
| 4,330,627 | 5/1982 | Thomas et al. ..................... 435/301 |

FOREIGN PATENT DOCUMENTS

| 73512 | 3/1983 | European Pat. Off. .............. 422/72 |
| 2067514 | 8/1971 | France ................................ 422/102 |

Primary Examiner—Michael S. Marcus
Assistant Examiner—Joseph P. Carrier
Attorney, Agent, or Firm—Sughrue, Mion, Zinn, Macpeak and Seas

[57] ABSTRACT

The conditioning device has a receptacle (5) which communicates with n calibrated analysis cells (10 to 19) in which the analysis reagents are place, the liquid to be analyzed being conveyed from the receptacle (5) towards the cells (10 to 19) by centrifuging. The device is in the form of a strip unit (1); the analysis cells (10 to 19) are preceded by tanks (20 to 29) of slightly larger volume, the cells (10 to 19) communicating with the tanks (20 to 29) via capillary orifices (30 to 39). At the time of centrifuging, the tanks are filled successively. The device is compact but allows a large number of analyses to be made rapidly.

9 Claims, 7 Drawing Figures

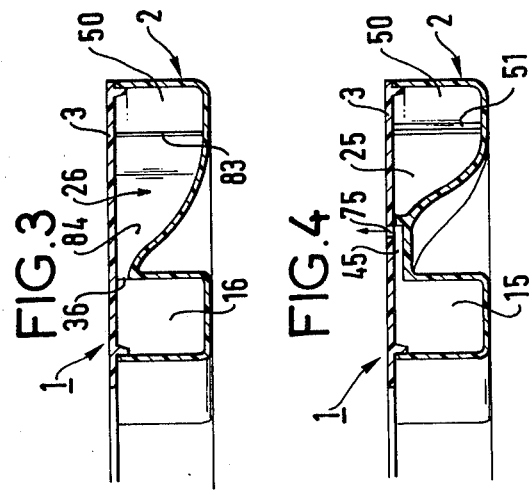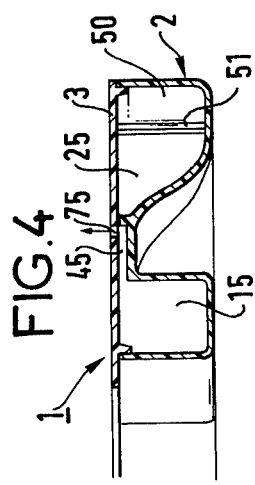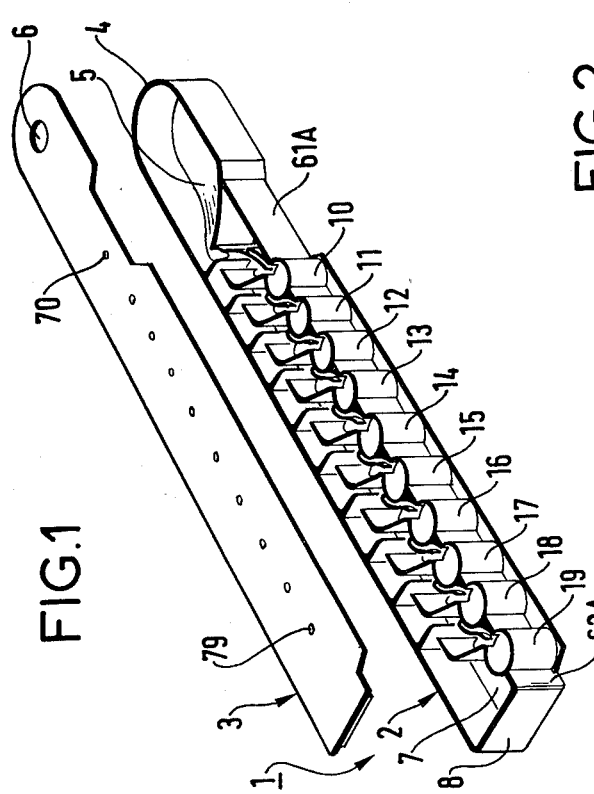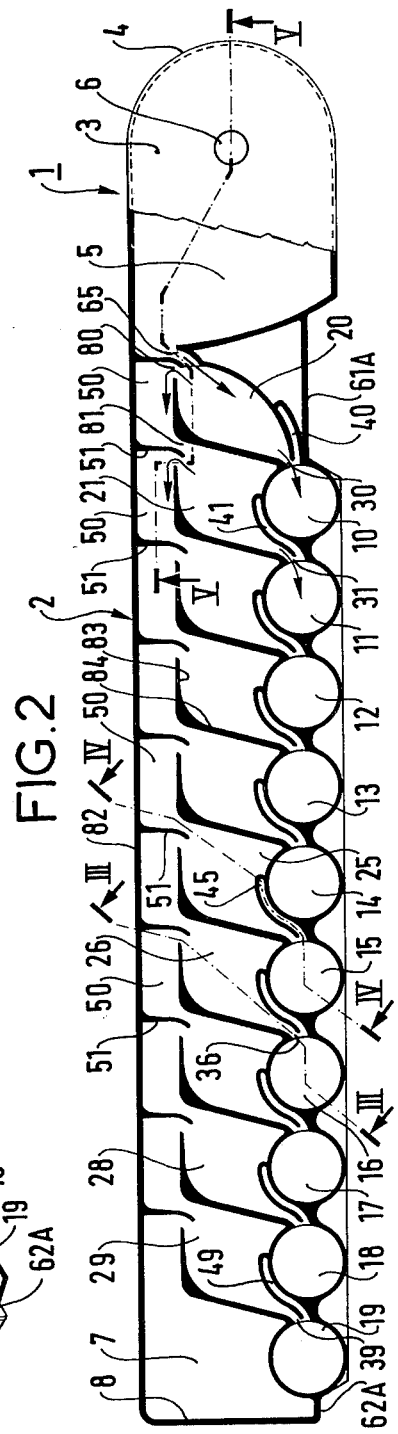

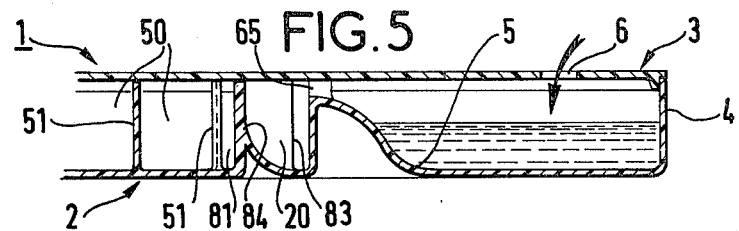
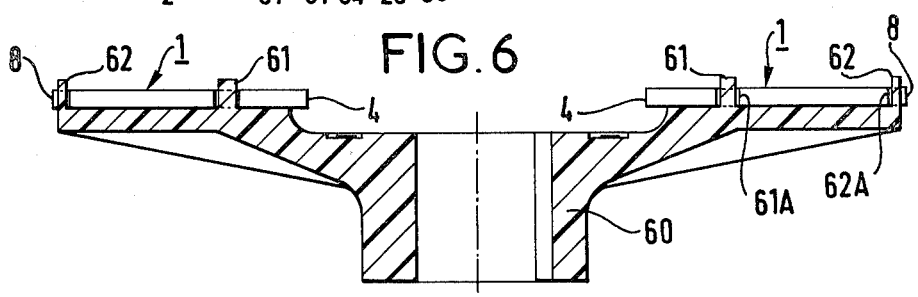
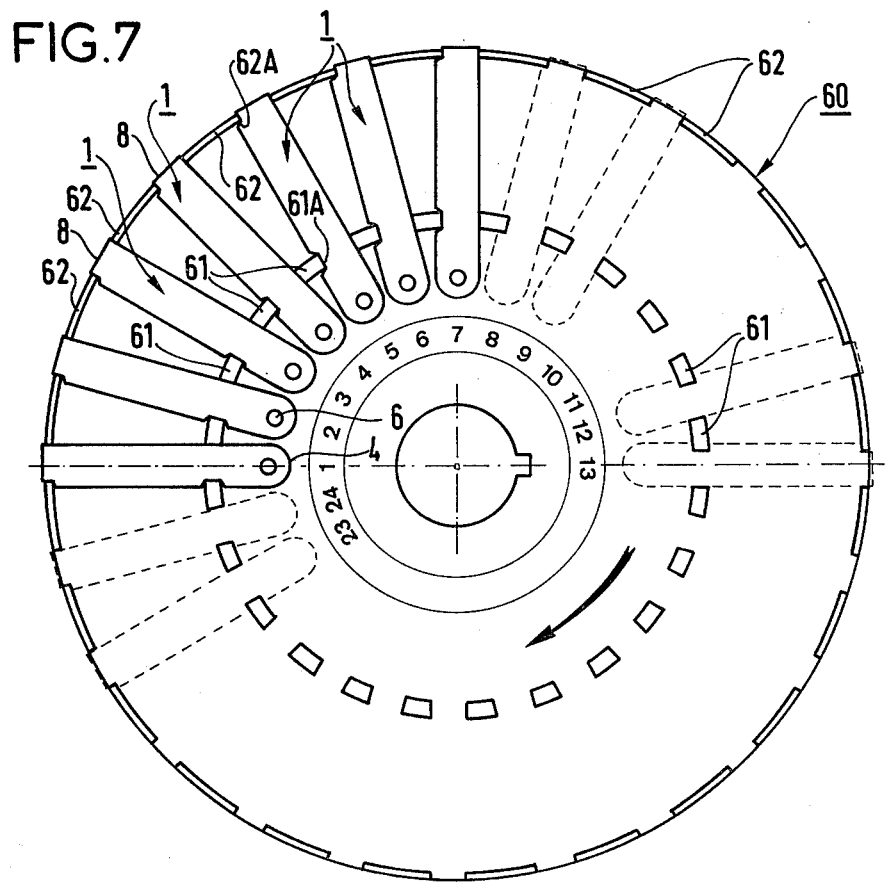

CONDITIONING DEVICE FOR PREPARING MULTIPLE ANALYSES

FIELD OF THE INVENTION

The invention relates to a conditioning device for preparing multiple analyses of an initial liquid sample to be analysed, said device comprising a receptacle which communicates with n calibrated analysis cells in which analysis reagents are inserted, the liquid to be analysed being conveyed from the receptacle to said analysis cells by centrifuging, each of the cells being provided with a capillary liquid-insertion orifice and an air exhaust capillary pipe.

BACKGROUND OF THE INVENTION

Presently known devices of this kind are in the form of disks, with the receptacle for the liquid to be analysed being located at the centre, of the disks, and n analysis cells being located around its periphery.

Therefore a single rotor can be used to perform only n simultaneous analyses with such a device.

Preferred embodiments of the present invention remedy this drawback and provide a device for preparing multiple analyses of an initial liquid sample, which device is of simple structure such that a plurality of such devices may be dealt with simultaneously on the same rotor, thereby saving, much space and time.

SUMMARY OF THE INVENTION

The invention provides a conditioning device for preparing multiple analyses of an initial liquid sample to be analysed, said device comprising a receptacle which communicates with n calibrated analysis cells in which analysis reagents are inserted, the liquid to be analysed being conveyed from the receptacle to said analysis cells by centrifuging, each of the cells being provided with a capillary liquid-insertion orifice and an air exhaust capillary pipe, the improvement wherein said device is in the form of a strip unit a first end of which carries said receptacle, said receptacle communicating with a first tank which communicates firstly with the first analysis cell via the capillary liquid-insertion orifice and secondly with a second tank which communicates firstly with a second analysis cell via the capillary liquid-insertion orifice and secondly with a third tank and so on, the $n^{th}$ tank which is in communication with the $(n-1)^{th}$ tank, communicating with the $n^{th}$ analysis cell via its capillary liquid-insertion orifice and with an overflow cell located near the second end of the strip unit, the volumes of the tanks being slightly greater than the volumes of the analysis cells to which they are respectively associated, the analysis cells as well as the tasks being substantially aligned along the strip unit, the communication means between the tanks being arranged so as to effect successive but not simultaneous filling thereof, said conditioning device being suitable for fixing on a rotary circular plate which forms a rotor and being placed along a radius of said plate, the strip unit end which is fitted with the receptacle being located near the centre of the plate, the end which is fitted with the overflow chamber being situated near the periphery of the plate.

BRIEF DESCRIPTION OF THE DRAWINGS

An embodiment of the invention is described by way of example with reference to the accompanying drawings in which:

FIG. 1 is a very schematic exploded perspective view of one embodiment of a device for preparing multiple analyses in accordance with the invention, the top part of the device being lifted up to show the internal structure of the device;

FIG. 2 is a longitudinal section through the device shown in FIG. 1;

FIG. 3 is a cross-section along line III—III of FIG. 2;

FIG. 4 is a cross-section along line IV—IV of FIG. 2;

FIG. 5 is a cross-section along line V—V of FIG. 2;

FIG. 6 is a cross-section of a rotary circular plate forming a rotor for carrying devices in accordance with the invention; and FIG. 7 is a plan view seen from above of the plate of FIG. 6.

MORE DETAILED DESCRIPTION

In the figures, reference 1 designates a conditioning device for preparing multiple analyses in accordance with the invention. It is substantially in the form of a strip which may, by way of a non-limiting illustration, be 5 to 6 centimeters in length, about one centimeter wide and about 5 mm thick.

In the embodiment illustrated, the device 1 is produced by assembling a part 2 which forms a housing and a part 3 which forms a cover.

In the neighbourhood of a first end 4 the housing 2 has a receptacle 5 in which the liquid to be analysed is inserted. For said purpose, the cover 3 has a suitable orifice 6.

The device has n analysis cells. In the example illustrated, said number n is 10 and the analysis cells are referenced 10 to 19.

Each of the analysis cells is preceded by a holding tank with a slightly larger volume than the cell. The holding tanks are referenced 20 to 29. For clearness' sake in the drawings only references 20, 21, 25, 26 and 29 are shown.

The analysis cells communicate with the holding tanks via respective capillary liquid-insertion orifices. These capillary orifices are referenced 30 to 39. For clearness' sake in the drawings, only references 30, 31, 36 and 39 are shown.

Also, each of the analysis cells is connected to a capillary air-escape pipe referenced 40 to 49 opening out in the cover 3 via an opening referenced 70 to 79. For clearness' sake in the drawings only references 40, 41, 45, 49, 70, 75 and 79 are shown.

The $n^{th}$ holding tank, namely tank 29 also leads into an overflow chamber 7 located near a second end 8 of the device 1.

On referring to FIGS. 1 and 2, it may be observed that in the device 1, the receptacle 5 leads via the pipe or orifice 65 into the first holding tank 20 which communicates firstly with the first analysis cell 10 via the capillary liquid-insertion orifice 30 and secondly with the second holding tank 21 via an orifice 80. Said tank 21 communicates firstly with the second analysis cell 11 via the capillary liquid-insertion orifice 31 and secondly with a third tank 22 via the orifice 81 and so on.

The last tank 29 which is fed by the tank 28 communicates firstly with the last analysis cell 19 via the capillary liquid-insertion orifice 39 and secondly with the overflow cell 7.

The analysis cell are substantially adjacent and aligned along the strip; the tanks are also aligned and adjacent. In the example illustrated, all the tanks communicate with a duct 50 delimited by a wall 82 of the housing 2 and walls 83 of the tanks substantially parallel to the wall 82. Said duct is provided with suitable baffle plates such as 51 which ensure successive and non-simultaneous filling of the holding tanks during operation which is described hereinafter. The communication orifices such as 80, 81 between said duct 50 and the various tanks are not capillary orifices. The tanks are delimited by the aforementioned walls 83 and by walls such as 84 which are substantially parallel to one another.

In FIG. 5, which is a cross-section along line V—V of FIG. 2, it can be observed that the receptacle 5 for receiving the liquid sample to be analysed has a curved profile whose upper portion is located in the neighbourhood of its point of communication with the tank 20, and that the pipe or communication orifice 65 provided at that point is not capillary.

In FIG. 3, which is a cross-section along line III—III of FIG. 2, it can be observed that the tanks (in the present case, the tank 26) have curved profiles whose top parts are located in the neighbourhood of the capillary orifice 36 for inserting liquid into the corresponding analysis cells 16.

FIG. 4, which is a cross-section along line IV—IV of FIG. 2 shows clearly the location of the capillary air-escape pipe which is in the present case the pipe 45 for the anaylsis cell 15 which opens out in the cover 3 via the opening 75.

As appears clearly in FIG. 1, the analysis cells in the example illustrated are cylindrical. They may have a diameter of about 3 mm and a height also of about 3 mm.

Appropriate reagents which can be dried or lyophilized are inserted into each of the analysis cells.

At least the walls which delimit the bottoms and tops of the analysis cells are transparent so as to allow a colorimetric analysis.

The strip-form analysis preparation device in accordance with the invention is designed to be fixed on a rotating circular plate which forms a rotor.

In FIG. 6 and 7, reference 60 designates such a plate rotated by means which are not shown.

The devices 1 are disposed along radii of said plate 60, the ends 4 which carry the receptacles being located near to the centre of the plate 60 while the ends 8 which carry the overflow chambers 7 are located near to the periphery of the plate 60.

The devices 1 are fixed on the plate 60 by any suitable means; by way of a non-limiting illustration, in the embodiment illustrated, the plate 60 is provided with chocks 61 and 62 which fit into position in suitable recesses 61A and 62A on the devices 1.

In this way, a large number of devices 1 in accordance with the invention may be fixed on the rotary plate 60 and their locations on the plate 60 may be numbered, as shown.

The analysis apparatus operates as follows:

After fixing the devices 1 on the rotary plate 60, various samples of liquid to be analysed are placed in the receptacles 5 via the orifices 6.

Said samples are inserted in the receptacles by any suitable means, e.g. by pipettes.

The rotor is then made to rotate.

In each of the devices 1, the liquid in the receptacle 5 is discharged towards the first holding tank which is rapidly filled, then the liquid passes through the second tank while the liquid in the first tanks is injected more slowly into the first analysis cell due to the capillarity of the communication orifice between said first tank and the first analysis cell.

Said process is repeated from one tank to the next and from each tank to its analysis cell.

Thus, when the second tank has been rapidly filled the liquid passes into the third tank while the second analysis cell is filled slowly.

When the last tank is full, the excess liquid passes into the overflow chamber while the last analysis cell is being filled slowly.

For a device having ten cells which have the aforementioned dimensions, i.e. each having a volume of about 21 mm$^3$, a liquid sample of about 0.3 cm$^3$ is inserted into the receptacle.

For a plate rotation speed of about 200 r.p.m., it is observed that the set of tank of a device in accordance with the invention is filled in less than 1 second whereas it requires about 2 or 3 seconds to fill the analysis cells.

As the cells are filled with liquid to be analysed air escapes through the capillary pipes.

When the rotor comes to a standstill, all the analysis cells are completely filled and there remains a little excess liquid in the holding tanks as well as in the overflow chamber. Colorimetric measurements can then be made.

I claim:

1. A conditioning device for preparing multiple analyses of an initial liquid sample to be analysed, said device comprising a receptacle, means communicating said receptacle with n calibrated analysis cells in which analysis reagents are inserted, the liquid to be analysed being conveyed from the receptacle to said analysis cells by centrifuging, each of the cells being provided with a capillary liquid-insertion orifice and an air exhaust capillary pipe, the improvement wherein; said device is in the form of a strip unit, said unit including a first end which carries said receptacle, and wherein said communication means includes a first tank which communicates firstly with the first analysis cell via the first capillary liquid-insertion orifice and secondly with a second tank which communicates firstly with a second analysis cell via the second capillary liquid-insertion orifice and secondly with a third tank and so on, the n$^{th}$ tank which is in communication with the (n−1)$^{th}$ tank communicating with the n$^{th}$ analysis cell via the n$^{th}$ capillary liquid-insertion orifice and with an overflow cell located near the second end of the strip unit, the volumes of the tanks being slightly greater than the volumes of the analysis cells to which they are respectively associated, the analysis cells as well as the tanks being substantially aligned along the strip unit, the communication means between the tanks further including means for ensuring successive and not simultaneous filling thereof, said conditioning device being suitable for fixing on a rotary circular plate which forms a rotor and being placed along a radius of said plate, the strip unit end which is fitted with the receptacle being located near the center of the plate, the end which is fitted with the overflow chamber being situated near the periphery of the plate.

2. A device according to claim 1, wherein the receptacle has a curved profile whose top portion is located in the vicinity of the point where it communicates with the first tank.

3. A device according to claim 1, wherein said tanks have curved profiles whose top portions are situated in the vicinity of the capillary insertion orifices of the corresponding analysis cells.

4. A device according to claim 1, wherein the communication means between said tanks include ducts provided with transverse baffle plates.

5. A device according to claim 1, wherein the analysis cells are substantially adjacent to one another.

6. A device according to claim 1, wherein the tanks are adjacent to one another.

7. A device according to claim 1, wherein the analysis cells are substantially cylindrical.

8. A device according to claim 1, wherein the walls which delimit the bottoms and the tops of the analysis cells are transparent so as to allow colorimetric analysis.

9. A device according to claim 1, further including means which allow it to be fixed to the rotary circular plate.

* * * * *